United States Patent [19]

Han et al.

[11] Patent Number: 4,864,073

[45] Date of Patent: Sep. 5, 1989

[54] PROCESSES FOR CONVERTING METHANE TO HIGHER MOLECULAR WEIGHT HYDROCARBONS VIA SULFUR-CONTAINING INTERMEDIATES

[75] Inventors: Scott Han, Lawrenceville, N.J.; Robert E. Palermo, New Hope, Pa.

[73] Assignee: Mobil Oil Corporation, New York, N.Y.

[21] Appl. No.: 189,878

[22] Filed: May 3, 1988

[51] Int. Cl.$^4$ .............................................. C07C 2/02
[52] U.S. Cl. ................................. 585/943; 585/654; 585/930; 585/934; 585/900
[58] Field of Search ............... 585/943, 730, 654, 656, 585/654, 658, 730, 930, 934, 943, 900

[56] References Cited

U.S. PATENT DOCUMENTS

| | | | |
|---|---|---|---|
| 2,565,195 | 8/1951 | Bell | 260/609 |
| 3,894,103 | 7/1975 | Chang | 585/408 |
| 4,480,143 | 10/1989 | Chang | 585/460 |
| 4,543,434 | 9/1985 | Chang | 585/310 |
| 4,544,785 | 10/1985 | Withers | 585/654 |
| 4,620,057 | 10/1986 | Kimble | 585/654 |

*Primary Examiner*—William R. Dixon, Jr.
*Assistant Examiner*—James M. Hunter, Jr.
*Attorney, Agent, or Firm*—Alexander J. McKillop; Charles J. Speciale; Edward F. Kenehan

[57] ABSTRACT

There is provided a process for converting methane to higher molecular weight hydrocarbons. In a first step, methane is contacted with carbonyl sulfide in the presence of UV light under conditions sufficient to produce CH$_3$SH. This CH$_3$SH then contacted with a sufficient catalyst, such as a zeolite, especially ZSM-5, under conditions sufficient to produce hydrocarbons having two or more carbon atoms.

3 Claims, No Drawings

PROCESSES FOR CONVERTING METHANE TO HIGHER MOLECULAR WEIGHT HYDROCARBONS VIA SULFUR-CONTAINING INTERMEDIATES

BACKGROUND

This application relates to processes for converting methane to higher molecular weight hydrocarbons, wherein methane is initially reacted with carbonyl sulfide to produce $CH_3SH$ which is, in turn, converted to hydrocarbons having two or more carbon atoms.

Natural gas is abundently available and provides a power source as a combustible fuel. However, the use of natural gas as fuel is often inconvenient for reasons of storage and handling. Accordingly, it would be desirable to convert components of natural gas to more valuable hydrocarbons. For example, conversion of natural gas to a liquid fuel would obviate certain problems of storage and handling. The main component of natural gas is methane.

The Chang U.S. Pat. No. 4,543,434 describes, inter alia, a process for converting methane by the following steps:

$$CH_4 + 4S \longrightarrow CS_2 + 2H_2S$$

$$CS_2 + 3H_2 \xrightarrow{\text{Co or Ni}} CH_3SH + H_2S$$

$$CH_3SH \xrightarrow{\text{HZSM-5}} [CH_2] + H_2S$$

$$4H_2S \longrightarrow H_2 + 4S$$

where $[CH_2]$ represents one or more hydrocarbons having at least two carbon atoms. The entire disclosure of this Chang U.S. Pat. No. 4,534,434 is expressly incorporated herein by reference.

SUMMARY

According to an aspect of this application, there is provided a process for converting methane to higher molecular weight hydrocarbons, said process comprising the steps of:

(i) contacting methane with carbonyl sulfide in the presence of UV light under conditions sufficient to generate $CH_3SH$; and (ii) contacting said $CH_3SH$ of step (i) with a sufficient catalyst under conditions sufficient to produce hydrogen sulfide and a mixture of hydrocarbons having at least two carbon atoms.

EMBODIMENTS

Methane may be converted to higher molecular weight hydrocarbons, e.g., gasoline, by an integrated process scheme which involves initially using methane and carbonyl sulfide, COS, in the presence of a UV light source. Methane may be reacted with COS in the presence of an irradiating UV light source, e.g., Hg lamps of medium or high pressure, Xe or $D_2$ arc lamps, etc., to give predominantly aliphatic organo-sulfur products such as $CH_3SH$, etc. Those products in turn may be converted to higher hydrocarbons over, e.g., ZSM-5. The CO produced in the initial reaction may be converted to COS in a reaction with sulfur. The reaction scheme to produce net reaction A is as follows:

1. $CH_4 + COS \longrightarrow CH_3SH + CO$

2. $CH_3SH \longrightarrow [CH_2] + H_2S$

3. $CO + S \longrightarrow COS$

A. $CH_4 + S \longrightarrow [CH_2] + H_2S$

The hydrogen sulfide produced in reaction A may be processed by technology described in the following numbered reactions, leading to net reactions B and/or C:

4. $H_2S + \frac{1}{2}O_2 \longrightarrow S + H_2O$

B. $CH_4 + \frac{1}{2}O_2 \longrightarrow [CH_2] + H_2O$ or

5. $H_2S + n/2M \longrightarrow M_{n/2}S + H_2$

6. $M_{n/2}S \longrightarrow n/2M + S$

C. $CH_4 \longrightarrow [CH_2] + H_2$

Reaction 4 is typically run over a catalyst. The metal in reactions 5+6 is preferably Group VIII or VIB.

The COS required to convert methane in reaction 1 may also be generated from methane by reaction with sulfur to form carbon disulfide and subsequent hydrolysis.

The reaction of methane with carbonyl sulfide to produce $CH_3SH$ and carbon monoxide (Reaction 1) has been reported by Knight et al. (J. Am. Chem. Soc. 85, 2349, 1963) to give the stated products with good selectivity (81%) towards aliphatic organo-sulfur compounds. Examples of conditions for reacting methane with carbonyl sulfide include a temperature of from about $-100°$ C. to about $100°$ C. and a pressure of from about 0.1 atmosphere to about 2 atmospheres. The reaction may take place in a quartz reaction tube. UV light may be supplied by a medium pressure Hg arc lamp with a filter, shined onto a quartz reaction tube. The UV light source may provide light having a wave length of from about 2290 Angstroms to about 2550 Angstroms.

In addition to $CH_3SH$, other organosulfur compounds, such as $(CH_3)_2S$, may be coproduced in the reaction of methane with carbonyl sulfide.

Organosulfur compounds, such as $CH_3SH$ and $(CH_3)_2S$, may be contacted with a sufficient catalyst under conditions sufficient to produce hydrogen sulfide and a mixture of hydrocarbons having at least two carbon atoms. Examples of such reactions are described in the aforementioned Chang U.S. Pat. No. 4,543,434 and in the Audeh et al U.S. Pat. No. 4,265,735, the entire disclosure of which is expressly incorporated herein by reference. Similar reactions involving the production of gasoline are also described in U.S. Pat. Nos. 3,894,102 and 3,894,103, the entire disclosure of which are expressly incorporated herein by reference.

A preferred catalyst for converting organosulfur compounds to hydrocarbons, e.g., gasoline, is ZSM-5.

However, other zeolites, such as those having a Constraint Index of from 1 to 12, may also be particularly useful.

The members of a particular class of zeolites useful for converting organosulfur compounds have an effective pore size of generally from about 5 to about 8 Angstroms, such as to freely sorb normal hexane. In addition, the structure provides constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the particular class. Windows of 10-membered rings are preferred, although, in some instances, excessive puckering of the rings or pore blockage may render these zeolite ineffective.

Although 12-membered rings in theory would not offer the same amount of constraint as 10-membered rings, it is noted that the puckered 12-ring structure of TMA offretite does show some constrained access. Other 12-ring structures may exist which may be particularly useful.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g., less than 5 Angstroms. On the other hand, zeolites which provide relatively free access to the internal zeolite structure have a low value for the Constraint Index, and usually pores of large size, e.g., greater than 8 Angstroms. The method by which Constraint Index is determined is described fully in U.S. Pat. No. 4,016,218, incorporated herein by reference for details of the method.

Constraint Index (CI) values for some typical materials are:

|  | CI | (at test temperature) |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index provides a means for identifying those zeolites which are useful in the present organosulfur conversion. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utlized herein, while affording a useful means for characterizing the zeolites of particular interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein within the approximate range of 1 to 12.

In addition to the above-mentioned zeolites other suitable catalysts for converting organosulfur compounds to hydrocarbons may include certain amorphous materials and other crystalline materials, particularly catalytically active molecular sieve materials, such as SAPO materials, as described in the Lok et al U.S. Pat. No. 4,440,871, the entire disclosure of which is expressly incorporated herein by reference.

Especially when ZSM-5 is employed as the active component of the catalyst, the conversion of organosulfur compounds to hydrocarbons and hydrogen sulfide may take place at a temperature of fromm about 200° C. to about 650° C. and at a pressure of from about 0 to about 2000 psig.

The reaction of carbon monoxide with sulfur to produce carbonyl sulfide (Reaction 3) is reported to occur slowly with liquid sulfur and readily with the vapor (Kirk-Othmer), Encyclopedia Chem. Tech., 2nd Ed. Vol. 22, p. 109). Examples of conditions for this reaction of carbon monoxide with sulfur include a temperature of 500° C. or less and a pressure of from about 0 psig to about 500 psig. Alkaline catalysts may be used in this reaction.

As reported in Kirk-Othmer, Encyclopedia, Chem. Tech., 3rd Ed. Vol. 12, p. 969, carbon monoxide may also be reacted with hydrogen sulfide to produce carbonyl sulfide and hydrogen according to the reaction.

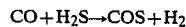

$$CO + H_2S \rightarrow COS + H_2$$

This reaction may take place over a CoS and NiS catalyst at 200° C. and atmospheric pressure.

Sulfur can be generated from hydrogen sulfide by the Claus process, wherein hydrogen sulfide is reacted with oxygen in the presence of alumina in accordance with the following reaction:

$$2H_2S + O_2 \xrightarrow{Al_2O_3} 2S + 2H_2O$$

Sulfur may also be obtained by the following reaction sequence:

$$2H_2S + 2(n/2M) \longrightarrow 2M_{n/2}S + 2H_2$$

$$2M_{n/2}S \longrightarrow 2(n/2M) + 2S$$

were M represents a suitable metal, e.g., a Group VIII or VIB metal. Examples of M include Fe, Co, Ni, Bi and Mo. This latter two-step reaction sequence for producing S is disclosed in the Chang U.S. Pat. No. 4,543,434. The reaction of hydrogen sulfide with metal may take place at temperatures between 0°–300° C. and at pressures between 0–2000 psig. The reaction of metal sulfide to regenerate metal and sulfur may take place at a temperature of from about 250° C. to about 1100° C. The sulfur produced may be recycled to produce carbonyl sulfide by reacting carbon monoxide with sulfur.

Whenever methane is used as a reactant as described herein, it may be used in pure form or essentially pure form in admixture with trace amounts of impurities. The methane may also be reacted in the presence of other inert or reactive gasses. For example, natural gas may be used as a source of methane reactant.

What is claimed is:

1. A process for converting methane to higher molecular weight hydrocarbons, said process comprising the steps of:

(i) contacting methane with carbonyl sulfide in the presence of UV light under conditions sufficient to generate CH₃SH; and (ii) contacting said CH₃SH of step (i) with a catalyst under conditions sufficient to produce hydrogen sulfide and a mixture of hydrocarbons having at least two carbon atoms.

2. A process according to claim 1, wherein CH₃SH is produced in step (i) in accordance with the stoichiometry set forth in the following reaction:

$$CH_4 + COS \rightarrow CH_3SH + CO.$$

3. A process according to claim 1, wherein carbon monoxide generated in step (i) is reacted with elemental sulfur to regenerate further carbonyl sulfide reactant for step (i).

* * * * *